(12) United States Patent
Lehman et al.

(10) Patent No.: US 7,833,281 B2
(45) Date of Patent: Nov. 16, 2010

(54) METHOD AND APPARATUS FOR AUGMENTATION OF A SPHINCTER

(76) Inventors: Glen A. Lehman, 5880 Stafford Way, Indianapolis, IN (US) 46220-1419; Brian K. Rucker, 1148 Luke St., King, NC (US) 27021

(*) Notice: Subject to any disclaimer, the term of this patent is extended or adjusted under 35 U.S.C. 154(b) by 1191 days.

(21) Appl. No.: 11/300,911

(22) Filed: Dec. 15, 2005

(65) Prior Publication Data

US 2006/0142789 A1    Jun. 29, 2006

Related U.S. Application Data

(60) Provisional application No. 60/636,131, filed on Dec. 15, 2004.

(51) Int. Cl.
*A61F 2/04* (2006.01)
(52) U.S. Cl. ................ 623/23.7; 623/23.65; 623/23.72; 604/57
(58) Field of Classification Search .............. 623/23.65, 623/23.69, 23.7, 23.72; 606/200, 157; 604/57, 604/59, 60
See application file for complete search history.

(56) References Cited

U.S. PATENT DOCUMENTS

| | | | |
|---|---|---|---|
| 5,476,472 A * | 12/1995 | Dormandy et al. .......... | 606/151 |
| 6,228,039 B1 * | 5/2001 | Binmoeller ................. | 600/566 |
| 6,306,094 B1 * | 10/2001 | Joseph ........................ | 600/458 |
| 6,338,345 B1 * | 1/2002 | Johnson et al. ............. | 128/897 |
| 7,166,122 B2 * | 1/2007 | Aganon et al. .............. | 606/200 |
| 2003/0163146 A1 * | 8/2003 | Epstein et al. .............. | 606/157 |
| 2003/0188755 A1 * | 10/2003 | Milbocker .................. | 128/898 |
| 2003/0192558 A1 * | 10/2003 | Durgin ........................ | 128/898 |
| 2003/0212419 A1 * | 11/2003 | West ........................... | 606/157 |
| 2004/0241316 A1 * | 12/2004 | Dinkelborg et al. ........ | 427/2.25 |
| 2005/0113855 A1 * | 5/2005 | Kennedy et al. ............ | 606/185 |
| 2006/0094929 A1 * | 5/2006 | Tronnes ...................... | 600/104 |

* cited by examiner

*Primary Examiner*—Bruce E Snow
(74) *Attorney, Agent, or Firm*—Woodward, Emhardt, Moriarty, McNett & Henry LLP

(57) ABSTRACT

A system and method for delivering one or more implantable members, such as metal coils, via an introducer member, such as an endoscopic needle, into a space created within the submucosal layers of the LES to augment and bulk the sphincter to improve compliance in patients with gastroesophageal reflux disease. The implantable member comprises a first substantially straightened configuration when carried by the introducer member, whereby it assumes a more curvilinear or coiled configuration following deployment such that it expands against adjacent submucosal tissue, creating a bulge at the implantation site. In another embodiment, the implantable member can serve as an anchoring port for sutures or other elements introduced for gastroplication of the LES to create tissue folds that increase sphincter compliance. The implantable members may be configured to include an external portion that interconnects with an adjacent implantable member, thereby creating tension that also increases compliance of the LES.

34 Claims, 7 Drawing Sheets

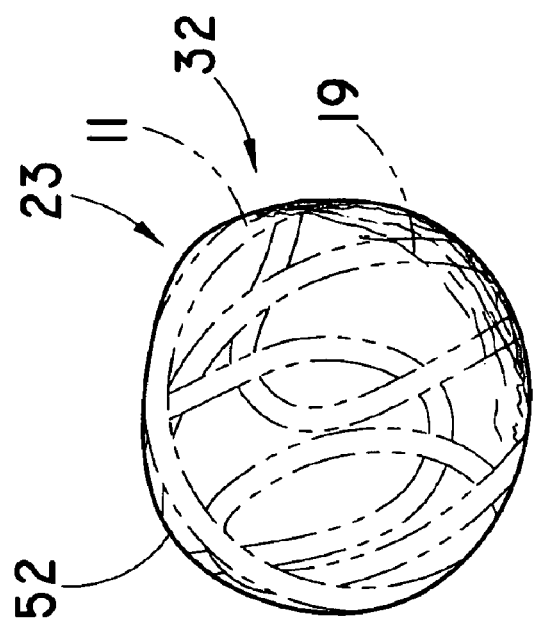
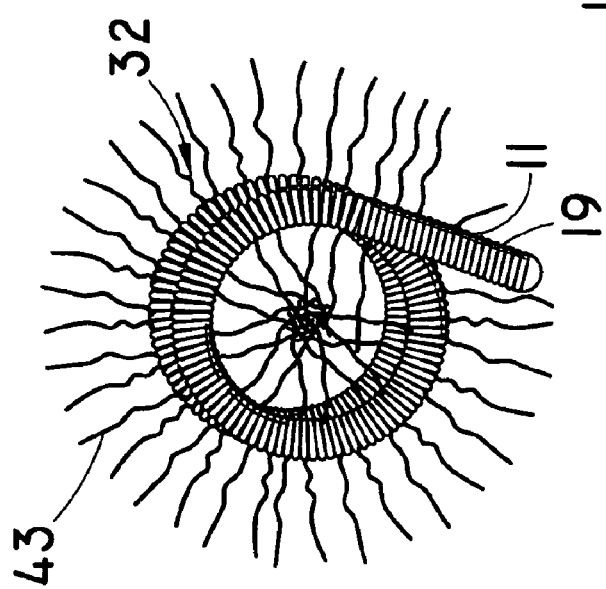
FIG. 2
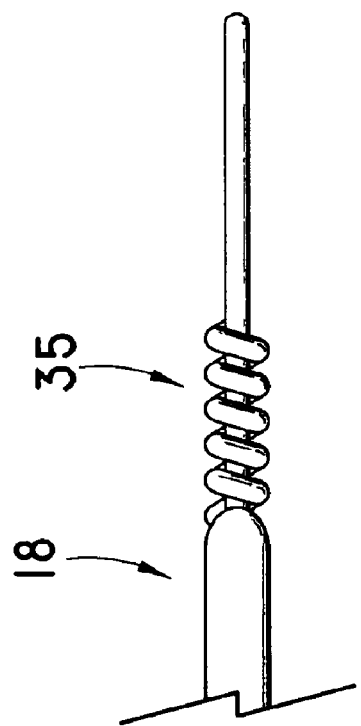
FIG. 2A
FIG. 3

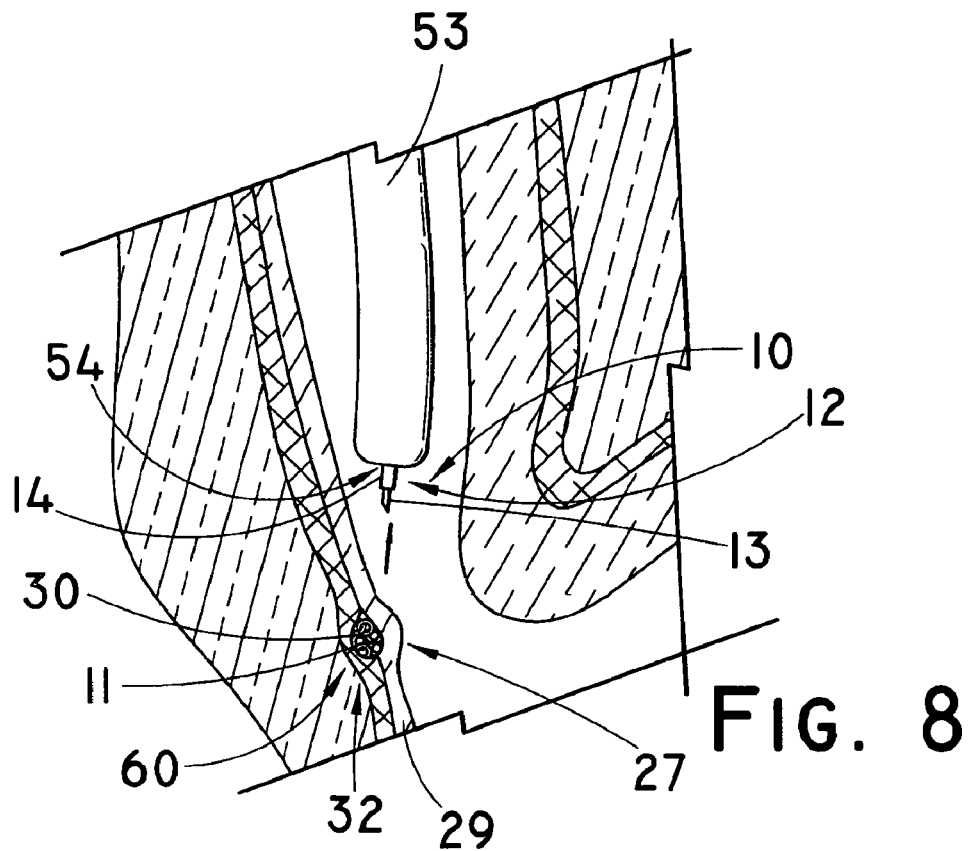
FIG. 8
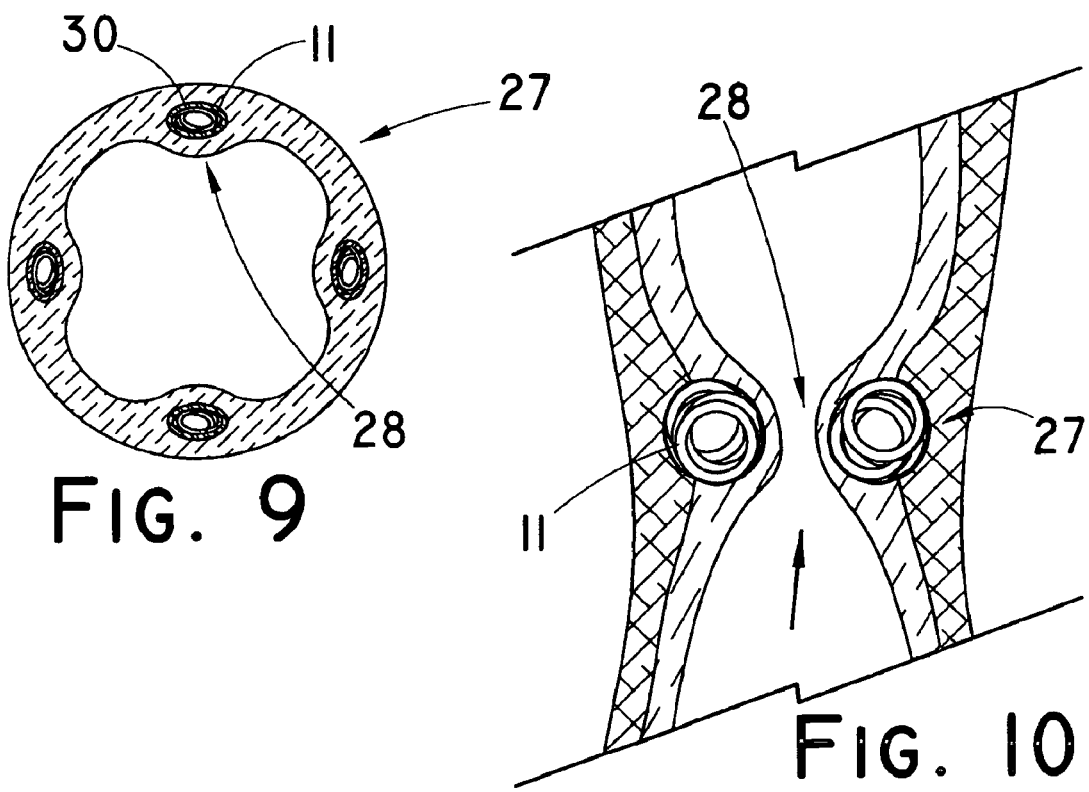
FIG. 9
FIG. 10

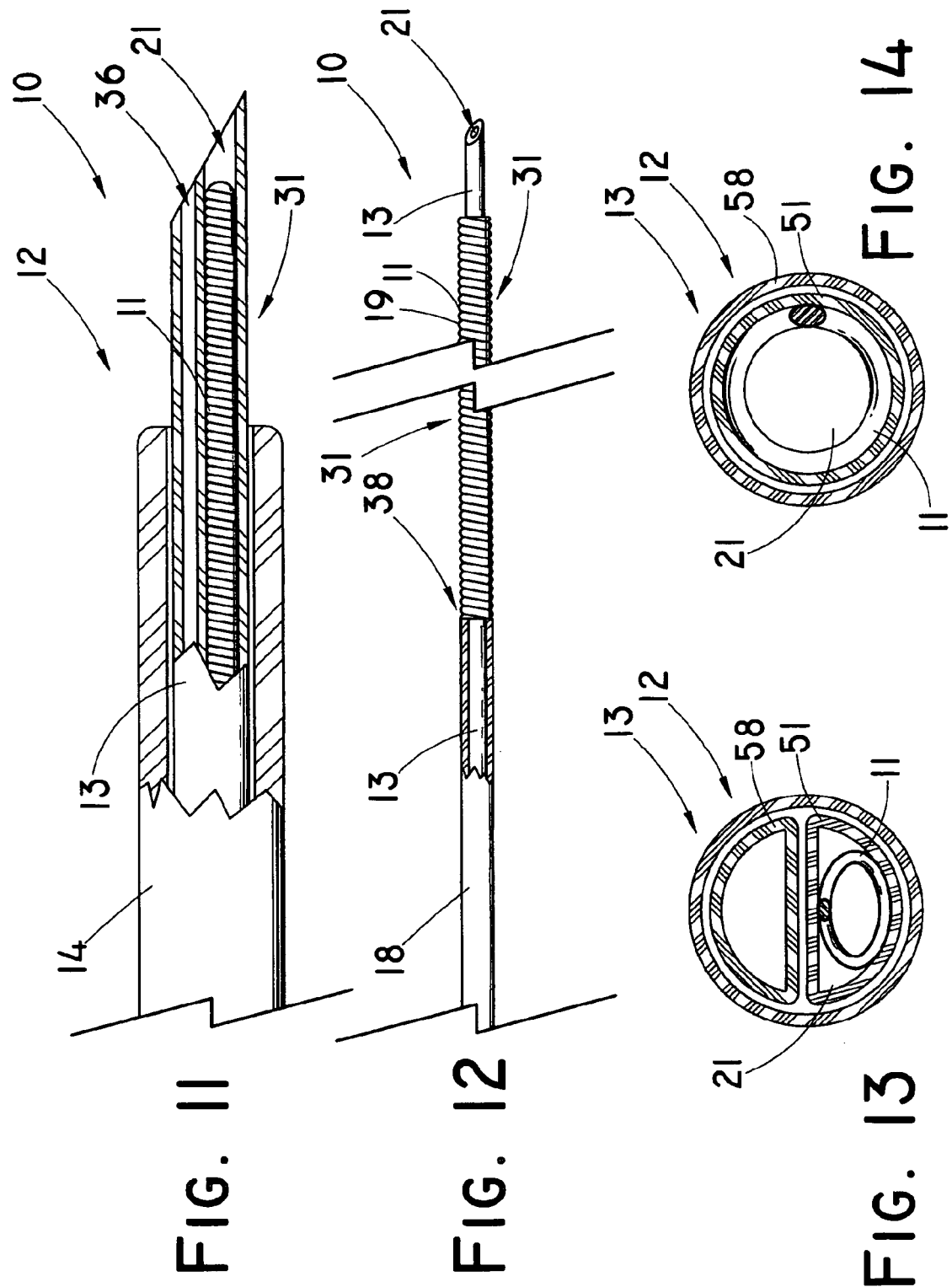

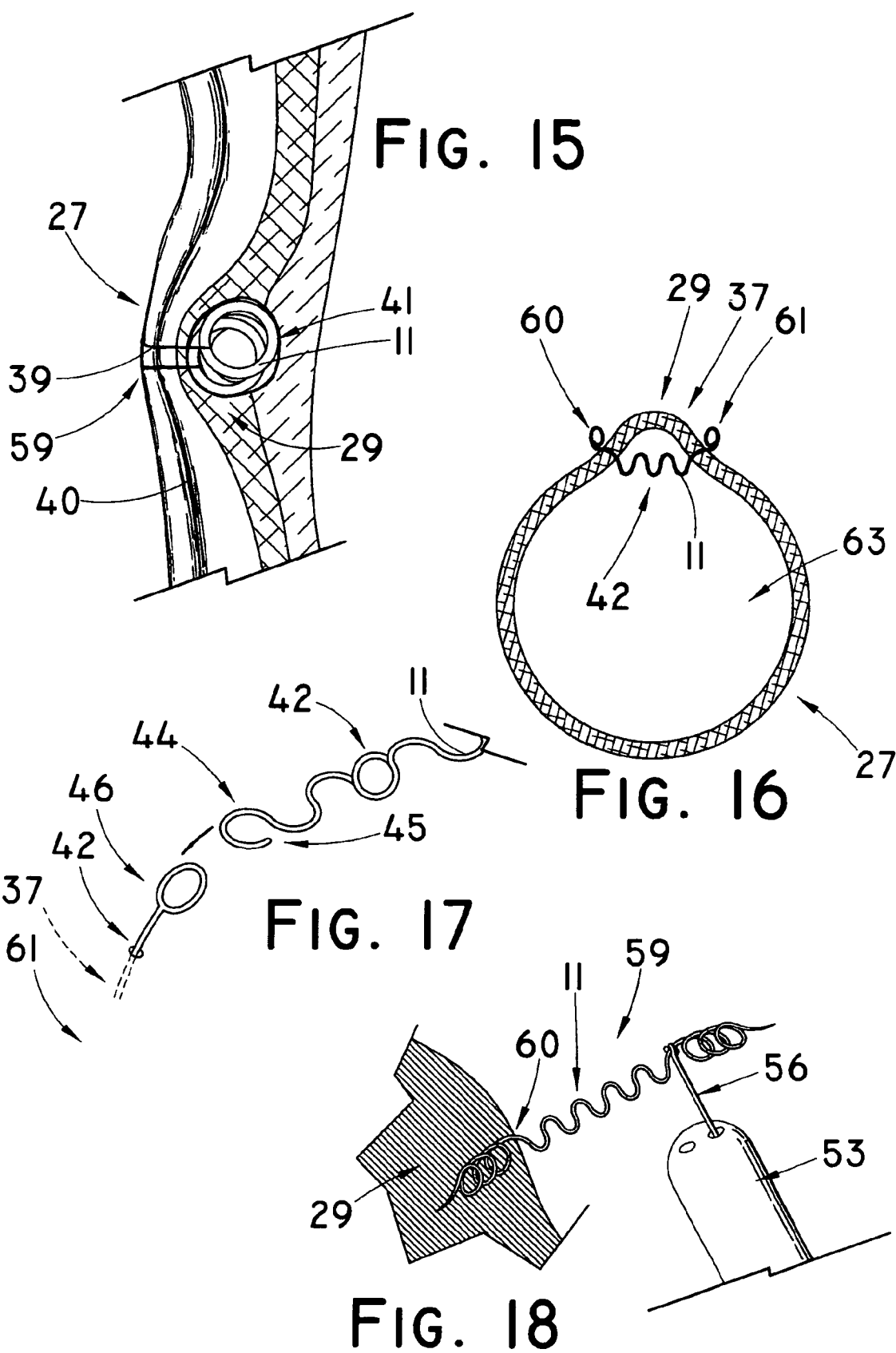

METHOD AND APPARATUS FOR AUGMENTATION OF A SPHINCTER

CROSS-REFERENCE TO RELATED APPLICATIONS

This application claims priority of provisional application Ser. No. 60/636,131, filed Dec. 15, 2004.

TECHNICAL FIELD

This invention relates to medical devices, more particularly to implant materials used to augment the function of a sphincter, particularly those delivered endoscopically, such as by a needle.

BACKGROUND OF THE INVENTION

It has been estimated that 7 million Americans suffer from progressive gastroesophageal reflux disease (GERD) which is characterized by frequent episodes of heartburn, typically on at least a daily basis. Without adequate treatment, GERD can cause erosion of the esophageal lining as the lower esophageal sphincter (LES), a segment of smooth muscle located at the junction of the stomach and the esophagus, gradually loses its ability to function as the barrier that prevents stomach acid reflux.

While drug therapies, such as proton pump inhibitors, have become a viable option for many of those diagnosed with GERD, surgical treatment may be indicated for patients with more serious disease or those who do not wish to adhere to daily, potentially expensive drug regimes that keep the disease under control. One such surgical approach is the Nissen Fundoplication which involves wrapping a portion of the stomach around the LES for support, then suturing it into place. Obviously, this invasive open surgical procedure is indicated only for patients who do not respond to standard GERD medications or dietary changes.

More recently, less-invasive endoscopic surgical procedures have been developed to restore compliance to the LES. The first is a type of endoluminal gastroplication utilizing the Bard EndoCinch™ Endoscopic Suturing System (C. R. Bard, Inc., Billerica, Mass.) which involves a endoscopic apparatus that places a series of adjacent sutures in LES to form one or more pleats that improve the ability of the sphincter to restrict the back flow of acid into the esophagus. Modest improvement of LES function has been demonstrated, but at least one study found that overall the number of reflux incidents was unchanged and the improvement in gastroesophageal reflux (GER) was modest. The data suggests that the plications eventually begin to fail and are not able to create a permanent fusion between the gastric folds, thus reducing the effectiveness of the treatment over time. A second surgical option involves the use of radio-frequency energy to reduce patient symptoms associated with GERD. The Stretta® System (Curon Medical, Inc., Sunnyvale, Calif.) comprises a flexible catheter with needle electrodes and a control module which are used to create thermal lesions or scarring at the LES. Unlike endoplication treatment, which is most effective at reducing acid exposure when upright, the RF scarring acts to reduce supine acid exposure in treated patients. It is thought that neurolysis within the treated area acts to reduce acid sensitivity and disruption of the vagal mechanosensitive trigger that leads to GERD. It is this loss of sensitivity that is most likely responsible for symptom relief as little reduction in the pH profile has been found. Furthermore, many patients require more than one treatment to achieve positive results.

Laser ablation has also been studied in an animal model as a means to achieve scarring, but only moderate elevation of LES yield pressures was noted.

Another approach to treat GERD has been to inject or implant materials into the LES to bulk up and tighten the sphincter, thereby improving its functionality as a barrier to acid reflux. Collagen, PTFE paste, and plexiglass materials have been injected in human patients for LES augmentation, but studies have shown the benefits to generally decrease over time, requiring follow up treatments. One commercially available treatment, the Enteryx® Procedure (Boston Scientific Corp., Natwick, Mass.) involves the injection of an ethylene vinyl alcohol polymer (EVOH) in a dimethyl sulfoxide carrier within and along the muscle layer of the LES. As a foreign body, the injected polymer eventually becomes encapsulated by a fibrotic layer. Improvement in LES function is due to a decrease in muscle distensibility and increase in yield pressures. However, questions have arisen as to the safety of EVOH injections for treating GERD following the early clinical experience and the product was removed from the market in 2005. A similar system is the GATEKEEPER™ Reflux Repair System (Medtronic Inc., Minneapolis, Minn.) which involves endoscopically implanting a series of dry pellet-like prostheses made of a hydrogel, similar to that used to make contact lenses. Once implanted in tissue, the material gradually swells to about the size of a gelcap and exerts pressure on surrounding tissues, thereby bulking the LES and improving its integrity. A disadvantage of the aforementioned injectable/implantable materials is their complete lack of radiopacity makes it difficult to confirm correct placement under fluoroscopy, if so desired.

Despite progress being made in finding a efficacious endoscopic therapy for the treatment of GERD, a commercially available solution which has been demonstrated to be both safe and effective over the long term has, so far, proven to be elusive. The limitation of these procedures need to be addressed in a procedure that provides true, long-term augmentation of the LES that reduces patient GERD symptoms and decreases esophageal acid exposure.

SUMMARY OF THE INVENTION

The foregoing problems are solved and a technical advance is achieved in an illustrative apparatus for augmenting the lower esophageal sphincter (LES) and increasing compliance, the apparatus comprising one or more bulking members that are implanted into the submucosal layer of the LES via a delivery apparatus while is a first shape or configuration, whereby they assume a second, more curvilinear configuration upon deployment. The ability of the implantable member to assume the second configuration is due to the material properties thereof. Possible materials include using a metal, polymer, biomaterial, or composite thereof capable of holding a shape memory, such as certain grades of stainless steel; a superelastic or pseudoelastic material or alloy such as nitinol; or a plastically deformable material (e.g., malleable-grade stainless steel) that would allow the implantable member to deformed into an expanded shape as it is deployed, either as it is forced into contact with tissue within the implantation site, or by the assistance of a deforming member, such as a pusher disposed within the passageway of introducer member. The implantable members can comprise materials of varying radiopacity, depending on requirements for radiographic imageability. For example, to provide compatability with CT imaging, the present implantable member may be comprised of less radiopaque (or non-radiopaque) materials to avoid image distortion or reduce the amount of metal to the minimum required to ensure adequate shape memory or resiliency. In addition, the implantable member may advantageously comprise a distinct coloration or include visually contrasting striping or portions to enhance endoscopic visualization during placement.

In a first aspect of the present invention, the bulking members comprise coiled members, such as those similar to embolization coils, which assume a regular or irregular coiled configuration upon deployment that expands within the pocket created in the submucosa and expands against adjacent tissue such that a bulge is formed about the implantation site. The implantation of the bulking member to augment LES at this site, especially when in combination with additional implanted bulking members, increases the compliance of the sphincter. The bulking members may comprise any suitable material such as a stainless steel, or shape memory metal, alloy, or polymer (e.g., nitinol) and may further comprise attached fibers, outer polymer or biomaterial layers or coating, and/or pharmacologically active substances applied to or incorporated therewithin.

Delivery of the bulking members into the submucosa of the LES can be accomplished by any suitable means, such as an introduction member which might include a needle, catheter, etc., and a delivery apparatus to actuate the deployment of the bulking member. In one illustrative embodiment, the bulking member is deployed through the passageway of an endoscopic needle, such as a type similar to that used obtaining biopsy samples. The needle, which may be ultrasonically guided, extends from an outer sheath to penetrate the submucosa while a pusher member urges the bulking member from the passageway into a pocket formed in the submucosa. Additional bulking member may be delivered to the implantation site or sites located adjacent or opposite the first site. The apparatus may be configured or adapted to include a means to create a pocket in which to deliver the implantable member(s) may be delivered, either prior to loading of the bulking member, around the member, which may be tethered to the pusher/delivery member, or through a separate needle or lumen. The apparatus can include a proximal end adapted for connection to a fluid reservoir, such as a syringe to inject saline or another infusate. Alternatively, the fluid reservoir may be incorporated into the device or a mechanical means for creating a void space within the tissue may be incorporated into the device or employed as an ancillary device, e.g., a cutting or expandable device (e.g., balloon, basket) or an energy source to ablate tissue. In a related embodiment, the needle or other introduction member extends through the lumen of the bulking or coiled member as well as that of the pusher member which deploys the implantable member over the needle, which has prepared the implantation site prior to delivery.

In another aspect of the invention, the implantable member comprises an anchoring point for sutures during a gastroplication procedure to create folds at the LES to increase compliance. One of the disadvantages of gastroplication of the LES using sutures is that over time, the sutures may break or gradually erode through the tissue and pull free. When this occurs, the tissue fold created by the suturing procedure may be lost. To help prevent the sutures used to create the folds from being pulled free over time, the sutures may be looped around or through a single or combination of bulking/anchoring members or they may be tied or otherwise secured directly thereto. Alternatively, the bulking/anchoring members can be configured to serve as anchor points for other means of creating gastroplication folds, such as clips, staples, rings, etc.

In still another aspect of the invention, the implantable member, which is configured to provide a secure anchor within the submucosa layer, includes an external portion that extends outward through the mucosa layer where it is configured to attach to the external portion of a second implantable member implanted at a nearby site along the LES. By connecting the two external portions and implantable members, the respective implantation sites are resiliently biased toward one another to add compliance to the LES. The external portions of the first and second implantable members may comprise hooks, eyelets, clasps, screws, or other interlocking or compatible structure such that a connection can be made using an endoscopic tool or other means. Alternatively, the first and second implantable members can be joined by a single-piece external portion so that the first implantable member is implanted first and the second implantable member is embedded at an implantation site (e.g., using an endoscopic tool such as a forceps) at a distance from the implanted first member such that the correct amount of tension and compliance is attained.

BRIEF DESCRIPTION OF THE DRAWING

Embodiments of the present invention will now be described by way of example with reference to the accompanying drawings, in which:

FIG. 2 depicts a side view of an illustrative implantable member of the present invention comprising a coil having fibers attached thereto;

FIG. 2A depicts the distal end of the delivery/tethering apparatus for the embodiment of FIG. 2;

FIG. 3 depicts a side view of an implantable member of the present invention that assumes an irregular shape upon deployment;

FIGS. 6-8 depict a method for implanting an implantable member of the present invention to augment the lower esophageal sphincter;

FIG. 9 depicts a cross-sectional top view of the gastroesophageal junction with multiple implantable members implanted thereabout;

FIG. 10 depicts a cross-sectional side view of a lower esophageal sphincter of the present invention augmented by multiple implantable members of the present invention;

FIG. 11 depicts a partially sectioned side view of an embodiment of the present invention in which the needle portion includes a first lumen for delivery of an implantable member and a second lumen for infusing fluids;

FIG. 12 depicts a partially sectioned side view of an embodiment of the present invention in which the implantable member and pusher member are disposed over an inner needle portion;

FIGS. 13-14 depict cross-sectional end views of embodiments of the present invention in which the apparatus includes a first and a second needle portion;

FIG. 15 depicts a view of the gastroesophageal junction after gastroplication in which sutures are attached about implanted members of the present invention;

FIG. 16 depicts a cross-sectional view in situ in which the embodiment of the present invention comprises a first and a second anchoring member that are interconnected within the gastric lumen;

FIG. 17 depicts a view in situ of a first and a second anchoring member being attached to one another; and FIG. 18 depicts a view in situ on a first and a second anchoring member comprising a single interconnected member.

DETAILED DESCRIPTION

Figure 1:
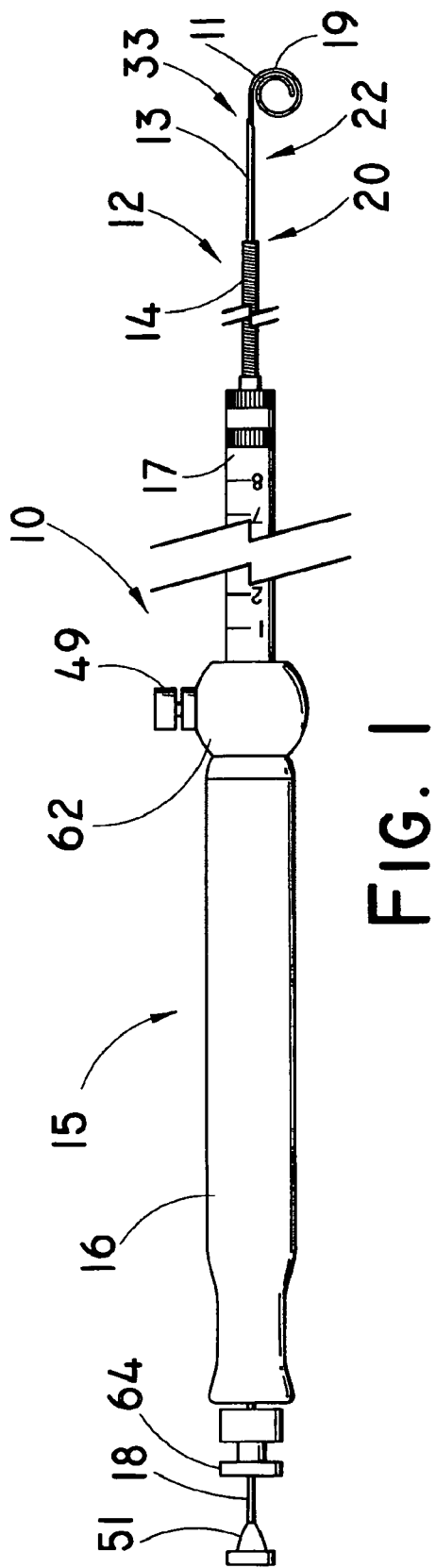
FIG. 1 depicts a side view of an illustrative implantable member and delivery system of the illustrative embodiment of the present invention.

The present invention, exemplary embodiments of which are depicted in FIGS. 1-18, includes an apparatus 10 and method for introducing one or more implantable members 11 using an introducer member 13, such as an endoscopic needle, into a pocket formed within the submucosal layer of the gastroesophageal (GE) junction or lower esophageal sphincter (LES) 27 to augment and tighten the LES to provide a more effective barrier against stomach acid reflux. In the illustrative embodiment depicted in FIGS. 1 and 1A, the apparatus 10 comprises a delivery system 12 that is similar in configuration to the ECHOTIP® Ultrasound Needle (Wilson-Cook Medical, Inc.), which includes a needle portion 33 (e.g., 19 ga), typically having a beveled distal tip 33, that is extendable from an outer sheath portion 14 (comprised of a coiled sheath member in this particular embodiment), each of which are attached to a coaxial handle assembly 15. The coaxial handle assembly 15 comprises a first portion 16 attached to the needle portion about the proximal end 48 thereof and a second, inner portion 17 that attaches to the coaxial outer sheath 14. The needle portion 13 includes an outer surface having enhanced ultrasonically reflectivity 50, which in the illustrative embodiment is accomplished by the addition of a pattern of indentations about the distal portion 22 thereof that aid in maneuvering and positioning the tip under ultrasound imaging (in conjunction with or as an alternative to positioning the needle using endoscopic guidance). An adjustable stop 62 disposed along the inner member is configured such that the set screw 49 can be engaged thereagainst to limit axial movement of the needle portion 13 relative to the sheath 14. The adjustable stop 62 controls how far the needle portion may extend beyond the distal end 20 of the sheath. The needle portion or introducer member 13 includes a passageway 21 sized to receive one or more implantable members 11, such as the illustrative coiled member 19. When the introducer member 13 has been advanced from the sheath and/or scope to penetrate the submucosal layer, the one or more implantable members 11 loaded therein are contacted by a slidable pusher member 18 or other means of urging the one or more implantable members from the passageway 21 and into a space or pocket created in the submucosal layer (as shown in later figures). The introducer member 13 may comprise a standard needle cannula (as depicted) comprising stainless steel or other suitable material. Alternative introducer members 13 could include a catheter having sufficient column strength to penetrate the LES and deliver the implantable member 11 (e.g, having a beveled, rigid nylon shaft or distal tip 33), or a more flexible catheter used in conjunction with a needle or other means to penetrate the LES and create a space for deployment. Alternatively, the distal portion 22 or distal tip 33 may comprise a metal cannula or portion while the remainder of the introducer member 13 comprises a polymeric catheter of sufficient stiffness to drive the distal needle tip portion into the submucosa. The illustrative pusher member 18, which is configured to deploy the implantable member from its constrained first configuration 31 (shown in FIG. 1A as that portion still inside the passageway) to a second, unconstrained configuration 32 (shown as the portion having exited the passageway), preferably comprises an elongate flexible member or stylet made of a material with adequate column strength, such as nylon, PEEK (PolyEtherEtherKetone), metal, etc., connected to a proximal hub 51; however, any suitable means of propelling and ejecting the implantable member from the passageway 21 may be used, including a guide wire, a spring mechanism or the injection of fluid (e.g., saline or air), etc. The illustrative helically coiled member 19 includes a configuration similar to a standard embolization coil or vascular occlusion device which are typically designed to be deployed into an artery to exclude or occlude an aneurysm, arteriovenous malformation, or other vascular abnormality. The coiled member, when deployed from a constrained substantially linear configuration, assumes a plurality of regular or irregular loops of coiled wire, typically comprising stainless steel, platinum, titanium, or another suitable material depending on requirements for radial strength and radiopacity. Less radiopaque materials, including those comprising composites and polymers are also contemplated. It should be noted that while the use of an endoscope and endoscopic needle represents a preferred method of visualizing the implantation site and delivering the implantable member into a pocket within the submucosal layer at the GE junction and LES, the configuration of the delivery apparatus used is not critical for an appreciation of the present invention.

Figure 5:
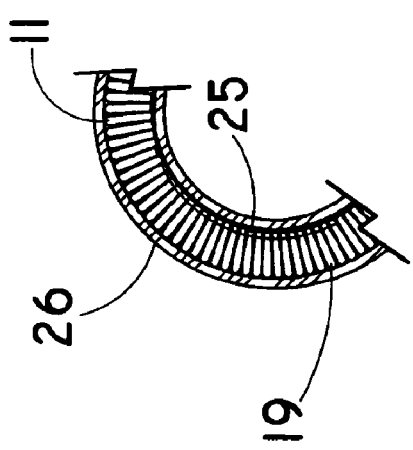
FIG. 5 depicts a side view of an implantable member of the present invention comprising a coiled member having an outer layer of a second material.
Figure 4:
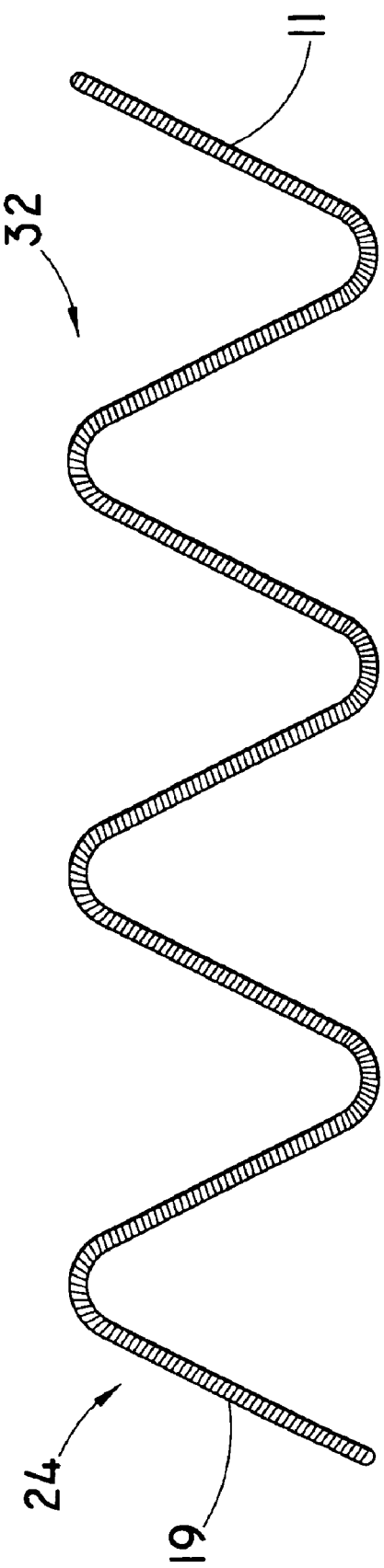
FIG. 4 depicts a side view of an implantable member of the present invention comprising a serpentine configuration.

FIGS. 2-5 depict additional implantable member 11 embodiments configured for deployment through the illustrative delivery system 12. FIG. 2 depicts a coiled member 19 that includes a plurality of attached fibers 20 made of a synthetic material (e.g, DACRON) or a biomaterial (e.g., collagen or extracellular collagen matrix) adapted to elicit a biological response such as tissue cell attachment, bioremodeling, thrombus formation, etc. The illustrative fibers 20, which are similar in configuration to those of the FLIPPER™ Detachable Embolization Coil (Cook, Inc., Bloomington, Ind.), may also be treated with a drug or other bioactive agent to bring about a desired biological response within the tissue pocket to improve augmentation, facilitate encapsulation, etc. Examples include, but are not limited to, thrombotic agents, anti-inflammatory agent, steroid, and growth factors. Bioactive agents may also be applied to or incorporated into the implantable member itself. FIG. 2A depicts a pusher member 18, similar to that used to deliver the FLIPPER™ Detachable Embolization Coil (shown in FIG. 2), that is configured to function as a tethering mechanism 35 to release and deploy the coiled member 19 in a more controlled manner than possible with the pusher member of FIG. 1. FIG. 3 depicts a coiled member 19 that assumes an irregular configuration 23 upon deployment, similar to the Gianturco-Grifka Vascular Occlusion Device (Cook Incorporated) and form a mass adapted to add bulk to the LES when in the unconstrained configuration 32. The illustrative coiled member 19 is shown enclosed in an optional constraining pouch 52 or bag into which it is deployed. The embodiment depicted in FIG. 4 comprises a coiled member 19 with a shape memory such that it resiliently assumes a serpentine configuration 24 upon deployment into the unconstrained configuration 32 that basically occupies one plane rather than coiling back on itself such as the embodiment of FIGS. 1-3. FIG. 5 depicts an implantable member 11 that comprises a core member 25 having an outer layer 26, such as the illustrative polymer sleeve or jacket enclosing the coil member 19. The outer layer 26 can comprise a shrink wrap sleeve or a coating that is dipped, sprayed, vapor deposited, electrostatically deposited, or otherwise applied to the surface of the core member 25 and may include a thermoelastic polymer, biodegradable polymer, collagen-based material, composite material, or other biocompatible material. The outer layer 26 can be mixed with a drug or bioactive agent that is released (gradually or as a bolus) therefrom or the layer can serve as a porous outer barrier to control the elution of the agent therethrough. In one exemplary embodiment, the core member can comprise a coiled nitinol wire member 19 encased in an outer layer 26 that acts to help protect against potential trauma caused by the wire and is configured to encourage encapsulation of the implantable member 11 over time. In another embodiment the entire implantable member 11 is made of a polymer having sufficient shape memory that allows it to resiliently assume a second curvilinear shape upon deployment from the needle. The implantable members 11 depicted represent only selected examples of deployable devices that are suitable for augmentation of the sphincter and it would be within the ability of one skilled in the medical arts to conceive of additional embodiments of the present invention. In another embodiment the outer surface 26 of the implantable member 11 comprises a lubricious material that facilitates deployment from the introducer member 13.

Figure 1A:
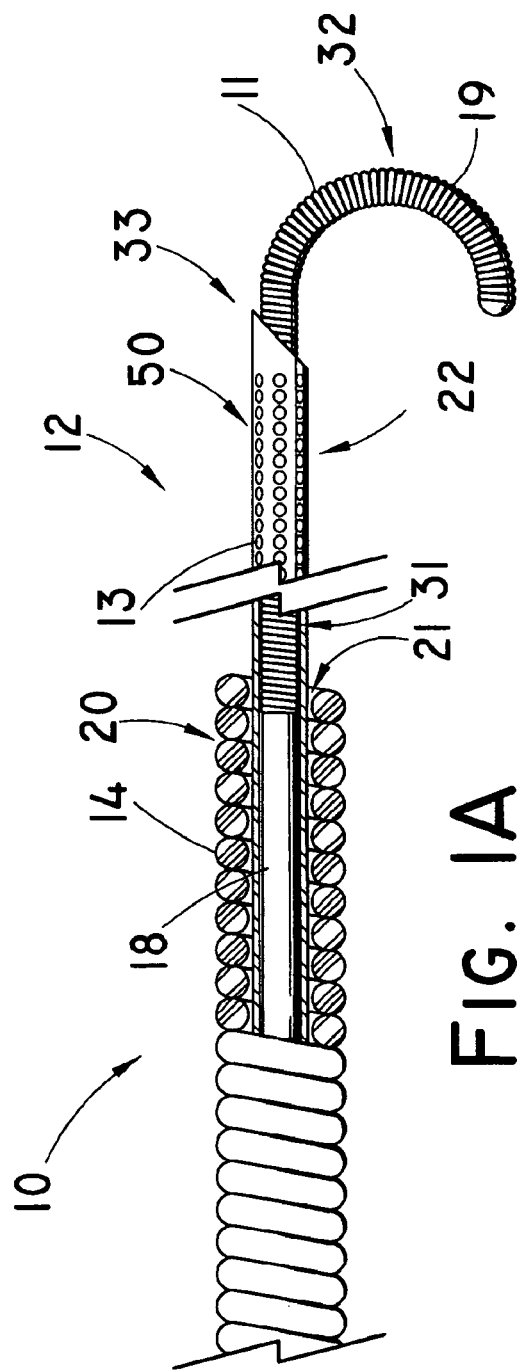
FIG. 1A depicts a partially sectioned side view of the distal portion of the embodiment of FIG. 1.
Figure 6:
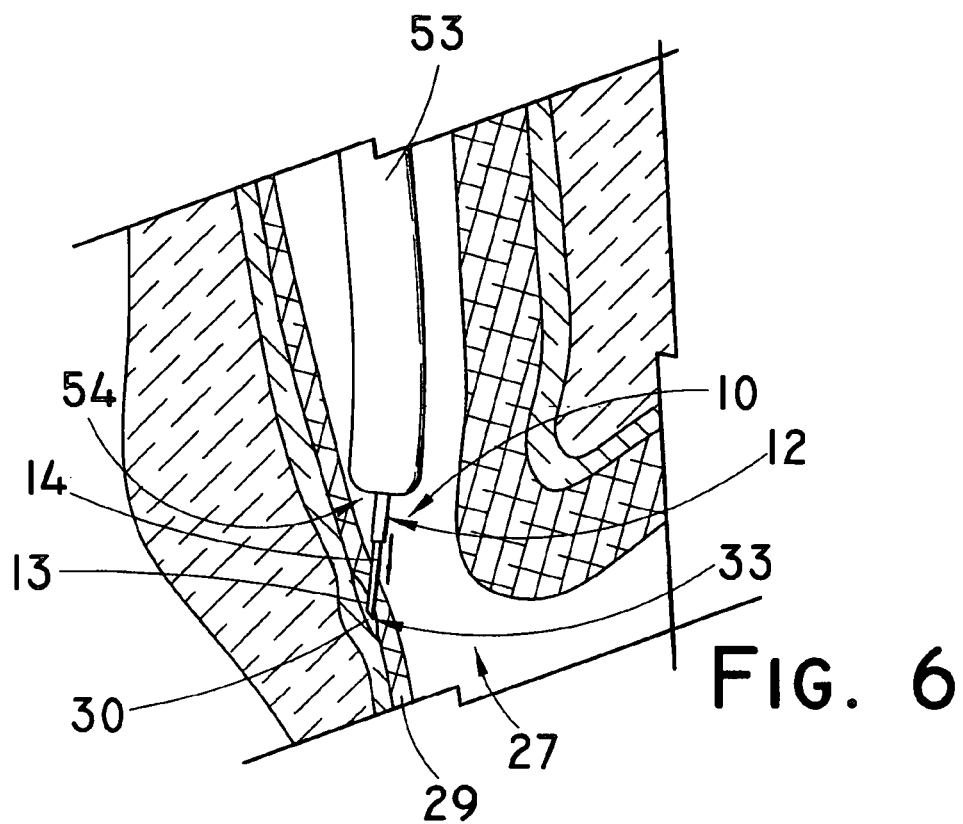
Figure 7:
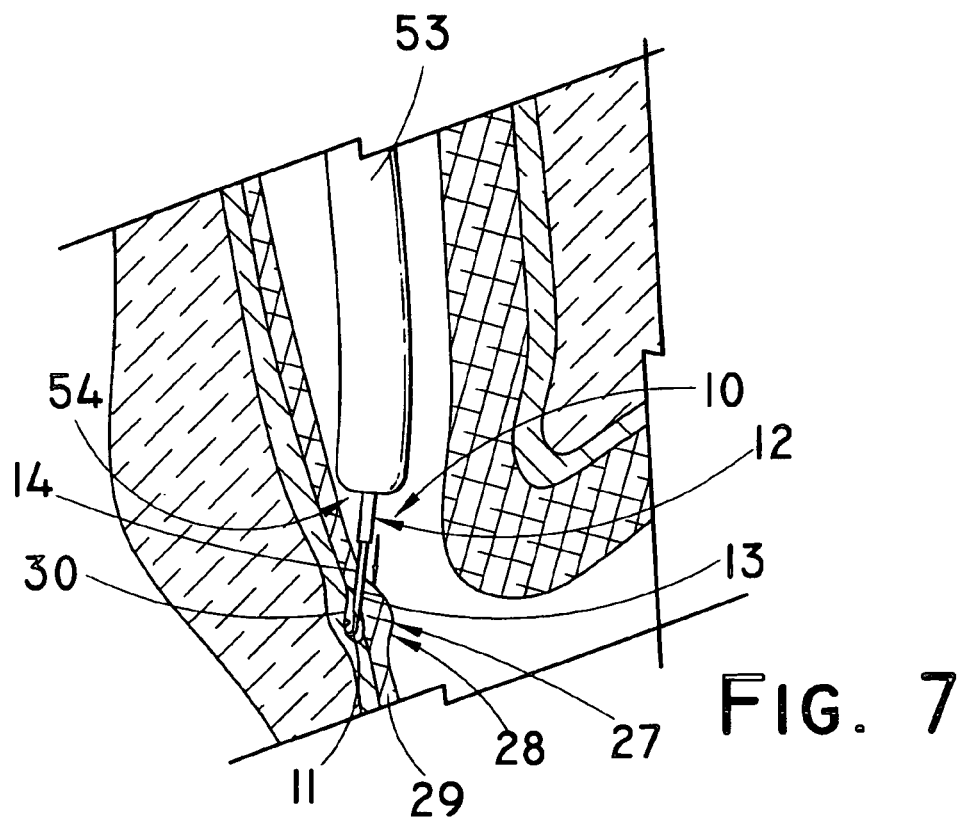

An endoscopic method for using the illustrative apparatus 10 of FIG. 1 to deploy one or more implantable members 11 to augment the LES is depicted in FIGS. 6-8. An endoscope 53, such as the illustrative gastroscope, is used to visualize the GE junction 27 (as depicted in FIG. 6). The apparatus 10 is introduced from the accessory or biopsy channel 54 and the needle 13 extended from the sheath portion 14 into the submucosal layer 29 with the needle tip 33 extending about 1-2 cm thereinto. Preferably, a pocket 30 is created by infusing saline or other infusate, the force of which helps separate the tissue layers with the submucosum. The infusate may be aspirated prior to deployment of the implantable member 11 into the pocket 30. As depicted in FIG. 7, a first implantable member 11 is then deployed from the needle 13 into the pocket 30 using the pushing member 18 depicted in FIG. 1, where it assumes its final, deployed configuration 32 once free of the passageway, as depicted in FIG. 8. As the implantable member 11 is deployed, it expands against the surrounding tissue to create a bulge 28 at the implantation site 60 thereby adding bulk to the LES 27 to improve sphincter compliance providing a more effective barrier against stomach acid reflux. The needle 13 is then fully withdrawn from the LES and the procedure may be repeated to implant one or more additional implantable members 11 at first site 60 and/or additional sites before the scope 53 and apparatus 10 are removed from the patient.

FIGS. 9-10 depict the deployment of multiple implantable members 11 for augmentation of the LES. In FIG. 9, implantable members 11 are shown deployed at a four different locations with the LES 27, approximately 90° with respect to one another. In a side view depicted in FIG. 10, an opposing pair of coiled members 19 are shown implanted an LES in which the compliance has been augmented their presence. Once implanted, the implantable members 11 would be expected to cause a foreign body reaction by the adjacent tissues that would result in the implantable members being encapsulated overtime by a layer 34 of fibrotic cell growth. When such a response occurs, the encapsulation layer should eventually isolate the implanted members and improve acceptance by the body over time. The number or implantation pattern of the implantable members 11 is not critical to appreciate the present invention and may be varied or later increased according to the amount of augmentation required such that the LES exhibits the desired amount of tension to allow easy passage of food while providing an effective acid reflux barrier Now referring to the basic implantation procedure depicted in FIG. 6, a submucosal space is typically created in advance of deployment of the implantable member 11 by infusing saline or another infusate into the submucosal tissue of the LES. This may be accomplished in a number of ways. The saline can be infused through the needle 13 via a syringe or other fluid-dispensing device that is attached to a proximal connector (e.g., luer lock hub 64 shown in FIG. 1) of the apparatus with the implantable member 11 being then advanced into the passageway 21 of introducer member 13 (e.g., with the pusher member 18) and positioned in the distal portion 22 for deployment (as depicted in FIG. 1). Alternatively, the needle passageway 21 can be sized such that there is sufficient space to infuse saline around the preloaded implantable member 11, which may be tethered to the pushing member or otherwise releasably attached to a portion of the delivery system so that once the pocket 30 is created and the implantable member 11 is introduced therein, the operator can release the implantable member for final deployment. A well-known tethering mechanism 35, such as the illustrative type used for the FLIPPER™ detachable embolization coil (FIG. 2A), can be used to deploy the embolization coil in situations when it is advantageous to maintain full control over deployment. Another technique of deploying a preloaded implantable member 11 would be to allow the infusate to simultaneously create a pocket 30 and force a preloaded, untethered implantable member thereinto, particularly if the passageway 21 is sized to allow sufficient infusate to enter the submucosal tissue in advance of the implantable member. It is also within the scope of the present invention to introduce the implantable member directly into the submucosal tissue without first creating a pocket by the infusion of saline or another fluid therein. This may be done by creating a space with the needle itself, particularly if the implantable member 11 is configured to have sufficient shape memory to assume the second, expanded configuration within the tissue without the benefit of a space being created beforehand in which expansion can occur. To better visualize the implantable member 11 under endoscopy during implantation, the metal can be colored (e.g., blue) to better contrast with the tissue and/or delivery apparatus, or the surface can include indicia, such as striping (e.g., shrink wrap), colored etching, etc., that is added to create a visually distinct or contrasting pattern.

An alternative apparatus 10 configured for deploying a preloaded implantable member 11 after introducing saline or other infusate to create a pocket is depicted in FIG. 11. The illustrative needle 13 comprises a first passageway or lumen 21 for receiving the implantable member 11 and pushing member (not shown), while a second, typically smaller lumen 36 is included for delivery of the infusate. This allows the infusate and implantable member 11 to be introduced sequentially or simultaneously without requiring a further step such as loading the implantable member in the system or manipulating a tethering mechanism prior to deployment. A similar approach is depicted in the embodiment of FIG. 13 in which the delivery system 12 includes a pair of needles or introducer members 13,58 where the second introducer member 37 is disposed adjacent to the needle portion 13 (first introducer member), rather than the needle portion 13 comprising a double-lumen cannula as in the embodiment of FIG. 11. The first needle portion 13 would typically be smaller than would a single needle embodiment if a second needle is used (e.g., 25 ga). As depicted, the first and second needle portions 13,58 can each comprise a complimentary cross-sectional profile such that they 'mate' with one another as they reside in the outer sheath 14 and as a unit, form an overall circular cross-sectional profile that reduces the amount of resistance with the sheath portion 14 during advancement or withdrawal of the needle portions 13,58. In a related embodiment depicted in FIG. 14, the first and second needles 13,58 comprise a coaxial arrangement with the smaller, inner needle 13 being sized and configured for delivery of the implantable member 11 and the outer needle 58 sized and configured to receive the inner member 13 while preferably leaving sufficient space between the inner needle and inner wall of the outer needle for the infusion of saline or other infusate therethrough. FIG. 12 depicts another embodiment of the present invention in which the implantable member 11 (comprising a coiled member 19 in the first configuration 31) is loaded over the introducer member 13, which comprises a needle, rather than deploying the implantable member through the introducer member/needle 13 as with the previous embodiments. The apparatus 10 further comprises a pusher member 18 that is also slidably disposed over the needle 13 and is sized to contact the implantable member 11 about the proximal end 38 thereof to urge it over the needle 13, the tip of which is typically embedded in tissue, such that pusher 18 causes the implantable member 11 to be deployed within the submucosa, such as within a pocket created by the needle and infusate. The apparatus 10 may include an optional outer member (not shown) to sheath the introducer member 13, introducer member 11, and pusher member 18 or the apparatus 10 can be introduced through an endoscope without an outer member. Furthermore, the pusher member 18 may optionally include a tethering or deployment mechanism that attaches to the implantable member 11 to control the release thereof.

The use of an implantable member 11 as an anchor point 41 to secure a suture 39 in an endoplication procedure, is depicted in FIG. 15. To help prevent a particular suture 39 from pulling free and losing the tissue fold 40 created by suturing to tighten the LES, the suture or sutures are looped around, tied to, or otherwise attached about the implantable or anchoring member 11 implanted in the submucosal layer. The suture 39 can comprise a continuous loop 55 that is anchored by adjacently placed implantable anchoring members 11, as depicted, or a single strand or length of suture can be affixed to one anchoring member and looped through the adjacent anchor, where it is pulled tight and tied off or otherwise attached to create the fold 40. Alternatively, the fold can be created about the implantation site of a single anchoring member 11 (FIG. 17) which comprises the entire anchor point 41, rather than a combination of anchoring members 11. The suture 39 passes through the tissue folds 40 and is affixed to the anchor point 41 with implantable member 11 lying just under the surface. The increased compliance of the LES may be due to a combination of implantable members 11 and tissue folds 40 formed by gastroplication sutures, or the implantable members 11 can be configured to primarily function as anchor points 41 and not cause significant outward distension of the LES by their implantation alone.

Another novel method of gastroplication using the illustrative implantable members 11 is depicted in FIGS. 16-18 in which the implantable or anchoring member 11 is implanted in the submucosa of the LES and includes an external portion 42 that extends outward through the mucosal tissue layer thereof. The first external portion 42 is then available to connect with the external portion of a second implantable member 37 that is strategically placed at a distance away from the first implantable member 11 (as shown in FIG. 17) such that when the first and second implantable members 11,37 are connected to one another, the interconnected external portions 42, which may comprise a coiled member 19 or other resiliently configured element, bias the LES toward a closed and compliant condition while allowing the LES to expand to accommodate the natural passage of solids or fluids therethrough. Preferably, the interconnected first and second implantable members 11,37 are sufficiently close to one another along the perimeter of the LES 27 (FIG. 16) such that the external portions 42 are positioned therealong rather than extending across the central portion of esophageal or gastric lumen 63 where they could interfere with the passage of food. Since the external portions 42 are exposed to foodstuffs and gastric contents, they should comprise a material or outer coating that is resistant to acids or other potentially degradative substances. In the embodiment of FIG. 17, the first implantable member 11 is implanted at a first location 60, the implantable member including a first attachment element 44 which comprises a hooked portion 45. The hooked portion 45 is preferably of sufficient rigidity such that it is able to couple with a second attachment element 46 that is located on the external portion 42 of a corresponding second implantable member 37 which is implanted by an appropriate means at a second location 61. By coupling the second attachment element 46, which in the illustrative embodiment comprises a loop 47, to the first attachment element 44, the implantation sites 60,61 are resiliently drawn toward one another by the tension supplied by the interconnected exposed portions 42, thereby tightening the sphincter 27 (FIG. 16). The illustrative implantable members 11 may include an outer layer of material about the exposed portions 42 that comprises a porous polymeric material (e.g., urethane) adapted to encourage tissue ingrowth, particularly about the site where the exposed portions 42 exit the tissue. The first and second attachment portions 44,46 can comprise any suitable type of connection mechanism or means that can allow the clinician to join the two exposed portions once the implantable members 11 have been implanted. These include, but are not necessarily limited to various hooks, snaps, eyelets, screws, magnets or other compatible, interlocking structure configured to allow the two ends of the attachment portions to reliably engage one another and withstand the forces and environment conditions to which they are subjected to during the life of the apparatus. The second implantable member can be preloaded and delivered using the same introducer member, introduced by reusing the same introducer member, or be introduced using a second introducer member. As depicted in FIG. 18, forceps 56 guided via an endoscope 53 or another endoscopic device may be used to join the two attachment portions 44,46 (shown in FIG. 17) or manipulate or anchor the second external portion into place and the second implantation site 61, the first implantable member 11 being typically delivered through an ultrasonically guided introduction member such that the other instrumentation, such as an endoscopic 56, is not necessary for that step.

The embodiment of FIG. 18 includes first and second implantable members 11,37 that are interconnected by a single interconnecting portion 59, rather than two separate portions that must be attached to one another in situ. The implantable member 11, which comprises a coiled member 19, is implanted much like the embodiment of FIG. 1 except that the second attachment element 46 remains in the introducer member or needle until the introducer member is withdrawn from the first implantation site. After the first implantable member 11 is implanted using the an needle/introducer member (not shown) or other implantation means (e.g., grasping it with the illustrative endoscopic tool 53). The external portion 42 and second implantable member 37 are secured by a forceps (as depicted) or other suitable device which is used to embed the second implantable member at a location from the first implantation site that causes the correct amount of tension to tighten the LES, while not causing it to become overly compliant. The second implantable member 37 should comprise a configuration, such as a helical anchor (as shown) or barbs, that allows it to be securely embedded in tissue without being introduced via an introducer member, such as using the illustrative forceps 56. Alternatively, one skilled in the art should be able to conceive of a specially design needle or other introduction means that could be designed to aid with the penetration of the submucosal layer to assist with embedding the implantable member 37 therewithin.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27$^{th}$ edition.

What is claimed is:

1. A medical apparatus for adding bulk to the lower esophageal sphincter of a patient, comprising:
    an elongate introducer member including a distal end configured for penetrating tissue and a first passageway extending therethrough;
    one or more resilient implantable members, each said implantable member being constrainable by the introducer member into an elongate first configuration from an expanded second configuration, the medical apparatus comprising a mechanism configured to urge the one or more implantable members from the introducer member into the tissue of the lower esophageal sphincter, the one or more implantable members being adapted to resiliently expand toward the expanded second configuration upon deployment from the introducer member, said one or more implantable members being configured to expand into static contact with surrounding tissue of the lower esophageal sphincter on implantation to push against the surrounding tissue of the lower esophageal sphincter, so that expansive force by said one or more implantable member on the tissue is in equilibrium with containing force exerted by the tissue on said one or more implantable member, the second configuration being substantially more curvilinear in shape than the first configuration,
    wherein said apparatus includes a means for separating tissue and creating a pocket within the submucosal layers sufficient for implantation of at least one of the one or more implantable members.

2. The medical apparatus of claim 1, wherein the introducer member comprises a coaxial outer sheath and a needle portion extendable therefrom, the needle member being sized and configured for introduction through an endoscope.

3. The medical apparatus of claim 1, wherein the proximal end of the apparatus is adapted for connecting a fluid reservoir that communicates with the first passageway for the infusion of fluids through the introducer member.

4. The medical apparatus of claim 1, further comprising a second passageway.

5. The medical apparatus of claim 4, wherein the second passageway communicates with an infusion port such that fluid may be infused from the distal end of the introducer member while at least one of the one or more implantable members is disposed within the first passageway.

6. The medical apparatus of claim 1, wherein the implantable member is preloaded in the first passageway.

7. The medical apparatus of claim 1, wherein the first passageway includes a plurality of implantable members disposed therein.

8. The medical apparatus of claim 1, further comprising a pusher member configured for deploying the one or more implantable members from the first passageway.

9. The medical apparatus of claim 1, wherein the implantable member comprises a coiled configuration when in the second configuration, said coiled configuration comprising said coil looped around on itself in a plurality of loops, said loops being in contact with each other.

10. The medical apparatus of claim 1, wherein the implantable member comprises a serpentine member in the second configuration.

11. The medical apparatus of claim 1, wherein the implantable member comprises an irregular shape in the second configuration.

12. The medical apparatus of claim 1, wherein the implantable member is adapted to retract in at least one dimension, while expanding in at least another dimension when deployed into the second configuration.

13. The medical apparatus of claim 12, wherein the change in the width to length ratio of the implantable member when deployed is greater than 50%.

14. The medical apparatus of claim 12, wherein the change in the width to length ratio of the implantable member when deployed is greater than 100%.

15. The medical apparatus of claim 12, wherein the change in the width to length ratio of the implantable member when deployed is greater than 1000%.

16. The medical apparatus of claim 1, wherein the implantable member comprises a superelastic material configured into a helically coiled structure.

17. A medical apparatus for introduction into the submucosal space of the lower esophageal sphincter of a patient, comprising:
    an elongate needle member and a coaxial outer sheath sized and configured for introduction through a flexible endoscope, the needle member including a distal end and a first passageway extending therethrough;
    at least one implantable member;
    wherein the at least one implantable member is constrainable into a first substantially linear configuration for introduction through the first passageway of the needle member, and in said first configuration said implantable member is substantially straight and has a substantially constant external diameter;

and wherein the at least one implantable member includes a shape memory such that it is adapted to assume a second configuration upon deployment from the needle member, the at least one implantable member comprising a plurality of bends such that it is adapted to create a volumetric expansion of the submucosal space when implanted therein, and wherein the assumption of said second configuration includes maintaining said external diameter as substantially constant while said implantable member curls into a plurality of loops, said loops in contact along at least a portion of their respective exteriors.

18. The medical apparatus of claim 17, wherein the needle member includes an outer surface configured for enhanced ultrasonic reflectivity, said configuration of said outer surface being non-mobile with respect to said needle member.

19. The medical apparatus of claim 1, wherein the implantable member is enclosed in a bag.

20. The medical apparatus of claim 1, wherein the implantable member includes a plurality of attached fibers extending therefrom.

21. The medical apparatus of claim 20, wherein said fibers are adapted to elicit a biological response within the sphincter tissue.

22. The medical apparatus of claim 2, wherein said coaxial sheath and needle portion have a length sufficient to move through an endoscope placed through the esophagus to the gastroesophageal junction.

23. The medical apparatus of claim 18, wherein said needle includes a pattern of indentations about a distal portion of said needle, said pattern of indentations providing said enhanced reflectivity.

24. The medical apparatus of claim 1, wherein in said second configuration said implantable member has approximately diametrically-opposed portions that are adapted to contact and keep separate portions of tissue of said sphincter when said implantable member is within said sphincter.

25. The medical apparatus of claim 1, wherein the implantable member comprises stainless steel or a superelastic alloy.

26. The medical apparatus of claim 18, wherein said outer surface has a plurality of flat surfaces linearly arranged that provide enhanced ultrasonic reflectivity.

27. A medical apparatus for adding bulk to the lower esophageal sphincter of a patient, comprising:

an elongate introducer member including a distal end configured for penetrating tissue and a first passageway extending therethrough;

one or more resilient implantable members, each said implantable member being constrainable by the introducer member into an elongate first configuration from an expanded second configuration, the medical apparatus comprising a mechanism configured to urge the one or more implantable members from the introducer member into the tissue of the lower esophageal sphincter, the one or more implantable members being adapted to resiliently expand toward the expanded second configuration upon deployment from the introducer member, said one or more implantable members being configured to expand into contact with tissue of the lower esophageal sphincter on implantation, so that force by said one or more implantable member on the tissue is in equilibrium with force exerted by the tissue on said one or more implantable member, the second configuration being substantially more curvilinear in shape than the first configuration, wherein at least one of said implantable members is configured to be anchored in the lower esophageal sphincter by piercing the lower esophageal sphincter with said at least one implantable member or a suture connected to said at least one implantable member.

28. The apparatus of claim 27, wherein the suture has a continuous loop that is anchored by adjacently placed implantable members.

29. The apparatus of claim 27, wherein the suture is a single length affixed to a first of said implantable members and looped through a second of said implantable members.

30. The apparatus of claim 27, wherein a first and a second of said implantable members each include a respective external portion, said external portions adapted to engage with each other when said implantable members are in tissue of the lower esophageal sphincter.

31. The apparatus of claim 30, wherein the external portion of the first implantable member is a hook portion and the external portion of the second implantable member is a loop portion, said hook portion and said loop portion being adapted to be coupled to thereby tighten the sphincter.

32. The apparatus of claim 27, wherein at least one of said external portions of said first and second implantable members comprises a material or outer coating that is resistant to degradative substances.

33. The apparatus of claim 27, wherein a first and a second of said implantable members are interconnected by a single interconnecting portion.

34. The medical apparatus of claim 17, wherein said at least one implantable member includes a coil having an unoccupied lumen throughout.

* * * * *